(12) United States Patent
Schugt et al.

(10) Patent No.: US 8,118,748 B2
(45) Date of Patent: Feb. 21, 2012

(54) IMPLANTABLE CAPACITIVE PRESSURE SENSOR SYSTEM AND METHOD

(75) Inventors: Michael A. Schugt, St. Paul, MN (US);
Keith A. Miesel, St. Paul, MN (US);
Jeremy W. Burdon, Minneapolis, MN (US); Eric H. Bonde, Victoria, MN (US)

(73) Assignee: Medtronic, Inc., Minneapolis, MN (US)

( * ) Notice: Subject to any disclaimer, the term of this patent is extended or adjusted under 35 U.S.C. 154(b) by 994 days.

(21) Appl. No.: 11/116,804

(22) Filed: Apr. 28, 2005

(65) Prior Publication Data
US 2006/0247539 A1 Nov. 2, 2006

(51) Int. Cl.
*A61B 5/02* (2006.01)
(52) U.S. Cl. .................... 600/486; 600/485
(58) Field of Classification Search .......... 600/486, 600/561
See application file for complete search history.

(56) References Cited

U.S. PATENT DOCUMENTS

| | | | |
|---|---|---|---|
| 4,040,118 A * | 8/1977 | Johnston | 361/283.4 |
| 4,177,496 A | 12/1979 | Bell et al. | |
| 4,207,604 A | 6/1980 | Bell | |
| 4,389,895 A | 6/1983 | Rud, Jr. | |
| 4,407,296 A | 10/1983 | Anderson | |
| 4,433,372 A | 2/1984 | Eichrodt et al. | |
| 4,485,813 A | 12/1984 | Anderson et al. | |
| 4,711,130 A | 12/1987 | Glas et al. | |
| 4,774,626 A | 9/1988 | Charboneau et al. | |
| 4,815,469 A | 3/1989 | Cohen et al. | |
| 4,901,197 A | 2/1990 | Albarda et al. | |
| 4,967,755 A | 11/1990 | Pohndorf et al. | |
| 4,991,283 A | 2/1991 | Johnson et al. | |
| 5,020,377 A | 6/1991 | Park | |
| 5,052,388 A | 10/1991 | Sivula et al. | |
| 5,085,213 A | 2/1992 | Cohen | |
| 5,129,394 A | 7/1992 | Mehra | |
| 5,137,019 A | 8/1992 | Pederson et al. | |
| 5,209,121 A | 5/1993 | Hafner | |
| 5,259,247 A | 11/1993 | Bantien | |
| 5,345,362 A | 9/1994 | Winkler | |
| 5,353,800 A | 10/1994 | Pohndorf et al. | |
| 5,417,717 A * | 5/1995 | Salo et al. | 607/18 |
| 5,490,323 A | 2/1996 | Thacker et al. | |

(Continued)

FOREIGN PATENT DOCUMENTS
WO WO03106952 A2 12/2003

OTHER PUBLICATIONS

M.L. Topfer, "Thick-Film Microelectronics: Fabrication, Design and Applications"; pp. 41-59, 1977.

(Continued)

*Primary Examiner* — Patricia Mallari
(74) *Attorney, Agent, or Firm* — Michael C. Soldner

(57) ABSTRACT

Embodiments of the invention provide systems and methods for an implantable capacitive pressure sensor. Some embodiments of the invention include a capacitive pressure sensor capsule comprising a substrate, a conductive plate functionally coupled to the substrate, a conductive diaphragm spaced from the conductive plate and functionally coupled to the substrate, a lid hermetically sealed against the substrate, and pressure sensing circuitry disposed within a volume generally defined by the lid and the substrate. Embodiments of the invention also include a lead provided with an implantable pressure sensor capsule and a method of manufacturing a capacitive pressure sensor capsule.

12 Claims, 13 Drawing Sheets

U.S. PATENT DOCUMENTS

| | | | |
|---|---|---|---|
| 5,544,399 A | 8/1996 | Bishop et al. | |
| 5,564,434 A | 10/1996 | Halperin et al. | |
| 5,843,135 A | 12/1998 | Weijand et al. | |
| 5,855,995 A * | 1/1999 | Haq et al. | 428/210 |
| 5,883,779 A | 3/1999 | Catanescu et al. | |
| 5,935,752 A | 8/1999 | Ueda et al. | |
| 6,125,291 A | 9/2000 | Miesel | |
| 6,144,866 A | 11/2000 | Miesel et al. | |
| 6,163,723 A | 12/2000 | Roberts et al. | |
| 6,171,252 B1 * | 1/2001 | Roberts | 600/485 |
| 6,208,900 B1 | 3/2001 | Ecker et al. | |
| 6,221,024 B1 | 4/2001 | Miesel | |
| 6,248,080 B1 | 6/2001 | Miesel et al. | |
| 6,252,759 B1 | 6/2001 | Lange et al. | |
| 6,278,379 B1 | 8/2001 | Allen et al. | |
| 6,351,996 B1 * | 3/2002 | Nasiri et al. | 73/706 |
| 6,516,808 B2 | 2/2003 | Schulman | |
| 6,580,946 B2 | 6/2003 | Struble | |
| 6,584,853 B2 | 7/2003 | Park et al. | |
| 6,595,064 B2 | 7/2003 | Drewes et al. | |
| 6,612,175 B1 | 9/2003 | Peterson et al. | |
| 6,658,940 B2 | 12/2003 | Burczyk et al. | |
| 6,666,826 B2 | 12/2003 | Salo et al. | |
| 6,675,654 B2 | 1/2004 | Hegner et al. | |
| 6,704,186 B2 | 3/2004 | Ishikura | |
| 6,725,724 B2 | 4/2004 | Gluck | |
| 6,770,377 B2 | 8/2004 | Hegner et al. | |
| 6,828,801 B1 | 12/2004 | Burdick et al. | |
| 2001/0001311 A1 * | 5/2001 | Park et al. | 600/561 |
| 2002/0151816 A1 | 10/2002 | Rich et al. | |
| 2004/0057589 A1 | 3/2004 | Pedersen et al. | |

OTHER PUBLICATIONS

J.D. Provance; "Performance Review of Thick Film Materials"; Insulation Circuits; Apr. 1977; pp. 33-33.

R. Mistler; "Tape Casting: The Basic Process for Meeting the Needs of the Electronics Industry"; Ceramic Bulletin; vol. 69, No. 6, 1990; pp. 1022-1026.

* cited by examiner

IMPLANTABLE CAPACITIVE PRESSURE SENSOR SYSTEM AND METHOD

FIELD SECTION

The disclosure relates to an implantable capacitive pressure sensor system and method.

BACKGROUND SECTION

Pressure sensors may be implanted into a patient for temporary or chronic use in a body organ or vessel. Implantable pressure sensors are useful for sensing blood pressure in a heart chamber. Traditionally, such pressure sensors had circuitry components in a housing separate from the sensor. This design caused the sensors to be relatively large because of the additional housing and associated interconnects between the sensor and the circuitry. Therefore, greater space was required within the organ or vessel. Further, such sensors have been designed such that they could generally not be manufactured by mass-production techniques.

BRIEF SUMMARY SECTION

Some embodiments of the invention include an implantable capacitive pressure sensor capsule comprising a substrate, a conductive plate functionally coupled to the substrate, a conductive diaphragm spaced from the conductive plate and functionally coupled to the substrate, a lid hermetically sealed against the substrate, and pressure sensing circuitry disposed within a volume generally defined by the lid and the substrate. Embodiments of the invention also include a lead provided with an implantable pressure sensor capsule. Such a lead may be in communication with a medical device. Further, the medical device may use the pressure information to determine or adjust a therapy. Some embodiments of the invention also include a method of manufacturing a capacitive pressure sensor capsule. Capacitive sensor capsules in accordance with some embodiments of the invention are relatively low profile and may be manufactured using mass-production techniques.

DETAILED DESCRIPTION OF THE ILLUSTRATED EMBODIMENTS

Figure 1:
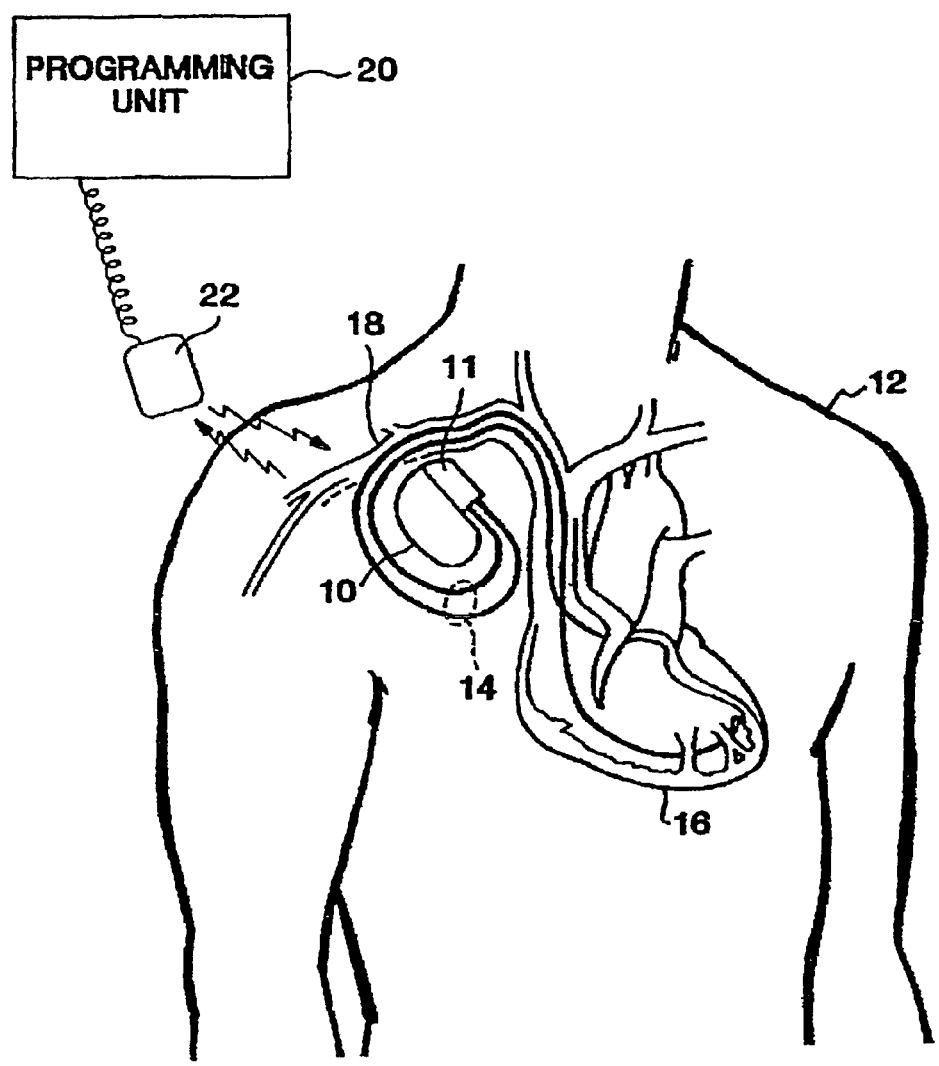
FIG. 1 is an illustration of a body-implantable device system in accordance with an embodiment of the invention.

The following discussion is presented to enable a person skilled in the art to make and use the embodiments of the invention. Various modifications to the illustrated embodiments will be readily apparent to those skilled in the art, and the generic principles herein may be applied to other embodiments and applications without departing from the spirit and scope of the present invention as defined by the appended claims. Thus, the present invention is not intended to be limited to the embodiments shown, but is to be accorded the widest scope consistent with the principles and features disclosed herein. The following detailed description is to be read with reference to the figures, in which like elements in different figures have like reference numerals. The figures, which are not necessarily to scale, depict selected embodiments and are not intended to limit the scope of the invention. Skilled artisans will recognize the examples provided herein have many useful alternatives, which fall, within the scope of the invention.

FIG. 1 illustrates an implantable medical device system adapted for use in accordance with the present invention. The medical device system shown in FIG. 1 includes an implantable device 10 (e.g., a pacemaker) that has been implanted in a patient 12. Device 10 is housed within a hermetically sealed, biologically inert outer casing, which may itself be conductive so as to serve as an indifferent electrode in the pacemaker's pacing/sensing circuit. One or more pacemaker leads, collectively identified with reference numeral 14 in FIG. 1 are electrically coupled to device 10 in a conventional manner and extend into the patient's heart 16 via a vein 18. Disposed generally near the distal end of leads 14 are one or more exposed conductive electrodes for receiving electrical cardiac signals and/or for delivering electrical pacing stimuli to heart 16. Leads 14 may comprise an elongated body having a lumen therein, and may be implanted with its distal end situated in the atrium and/or ventricle of heart 16.

Although the invention will be described herein in one embodiment which includes a pacemaker and leads implanted within the heart, those of ordinary skill in the art will appreciate that the invention may be advantageously practiced in connection with numerous other types of implantable medical device systems.

Also depicted in FIG. 1 is an external programming unit 20 for non-invasive communication with implanted device 10 via uplink and downlink communication channels. Associated with programming unit 20 is a programming head 22, in accordance with conventional medical device programming systems, for facilitating two-way communication between implanted device 10 and programmer 20. An example of a programmer 20 is described in U.S. Pat. No. 5,345,362, which is hereby incorporated by reference.

Figure 2:
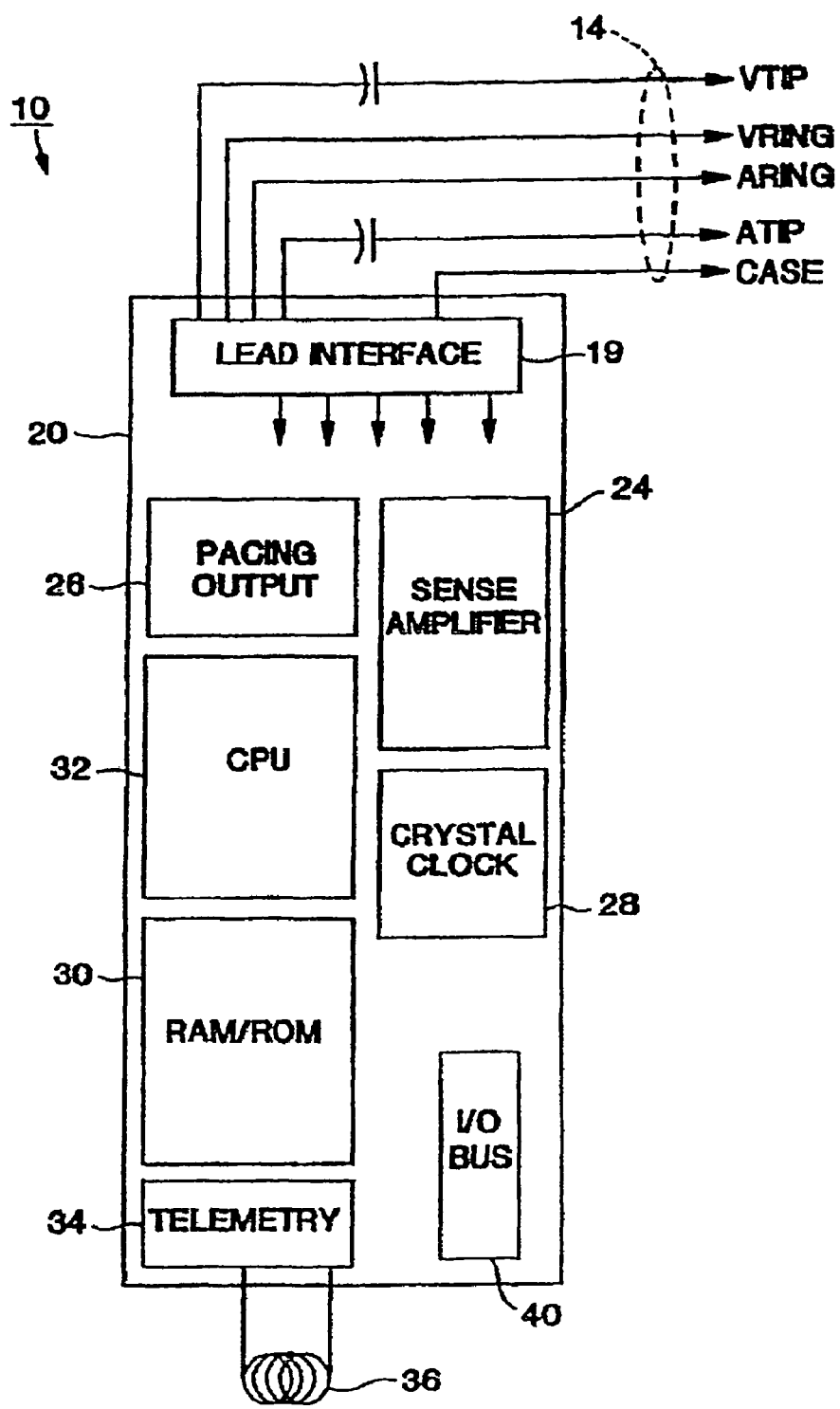
FIG. 2 is a block diagram of an implantable medical device in accordance with an embodiment of the invention.

FIG. 2 is a block diagram of an embodiment of electronic circuitry that makes up device 10. As can be seen from FIG. 2, device 10 comprises a primary stimulation control circuit 20 for controlling the device's pacing and sensing functions. The circuitry associated with stimulation control circuit 20 may be of conventional design, in accordance, for example, with what is disclosed U.S. Pat. No. 5,052,388, the contents of which is hereby incorporated by reference. Stimulation control circuit 20 may include sense amplifier circuitry 24, stimulating pulse output circuitry 26, a crystal clock 28, a random-access memory and read-only memory (RAM/ROM) unit 30, and a central processing unit (CPU) 32, all of which are well-known in the art. Device 10 may also include an internal communication circuit 34 so that it is capable communicating with external programmer/control unit 20.

With continued reference to FIG. 2, device 10 is coupled to one or more leads 14 which, when implanted, extend transvenously between the implant site of device 10 and the patient's heart 16, as previously noted with reference to FIG. 1. Physically, the connections between leads 14 and the various internal components of device 10 are facilitated by means of a conventional connector block assembly 11, shown in FIG. 1. Electrically, the coupling of the conductors of leads and internal electrical components of device 10 may be facilitated by means of a lead interface circuit 19 which functions, in a multiplexer-like manner, to selectively and dynamically establish necessary connections between various conductors in leads 14, including, for example, atrial tip and ring electrode conductors ATIP and ARING and ventricular tip and ring electrode conductors VTIP and VRING, and individual electrical components of device 10. For the sake of clarity, the specific connections between leads 14 and the various components of device 10 are not shown in FIG. 2, although it will be clear to those of ordinary skill in the art that, for example, leads 14 will necessarily be coupled, either directly or indirectly, to sense amplifier circuitry 24 and stimulating pulse output circuit 26, in accordance with common practice, such that cardiac electrical signals may be conveyed to sensing circuitry 24, and such that stimulating pulses may be delivered to cardiac tissue, via leads 14. Also not shown in FIG. 2 is the protection circuitry commonly included in implanted devices to protect, for example, the sensing circuitry of the device from high voltage stimulating pulses.

As previously noted, stimulation control circuit 20 includes central processing unit 32 which may be an off-the-shelf programmable microprocessor or micro controller, but in the present invention is a custom integrated circuit. Although specific connections between CPU 32 and other components of stimulation control circuit 20 are not shown in FIG. 2, CPU 32 may function to control the timed operation of stimulating pulse output circuit 26 and sense amplifier circuit 24 under control of programming stored in RAM/ROM unit 30.

In some embodiments, the invention includes an implantable capacitive pressure sensor capsule 100 as shown in various stages of assembly in FIGS. 3-11. The capacitive pressure sensor capsule 100 may comprise a substrate 110 (e.g., an insulative substrate), a conductive plate 120 functionally coupled to a first surface of the substrate 110, a conductive diaphragm 130 spaced from the conductive plate 120 and functionally coupled to the first surface of the substrate 110, a lid 140 hermetically sealed against a second surface of the substrate 110 opposite to the first surface, and pressure sensing circuitry 150 disposed within a volume generally defined by the lid 140 and the second surface of the substrate 110. Such a device may be disposed within lead 14 and/or be in communication with medical device 10.

Figure 5:
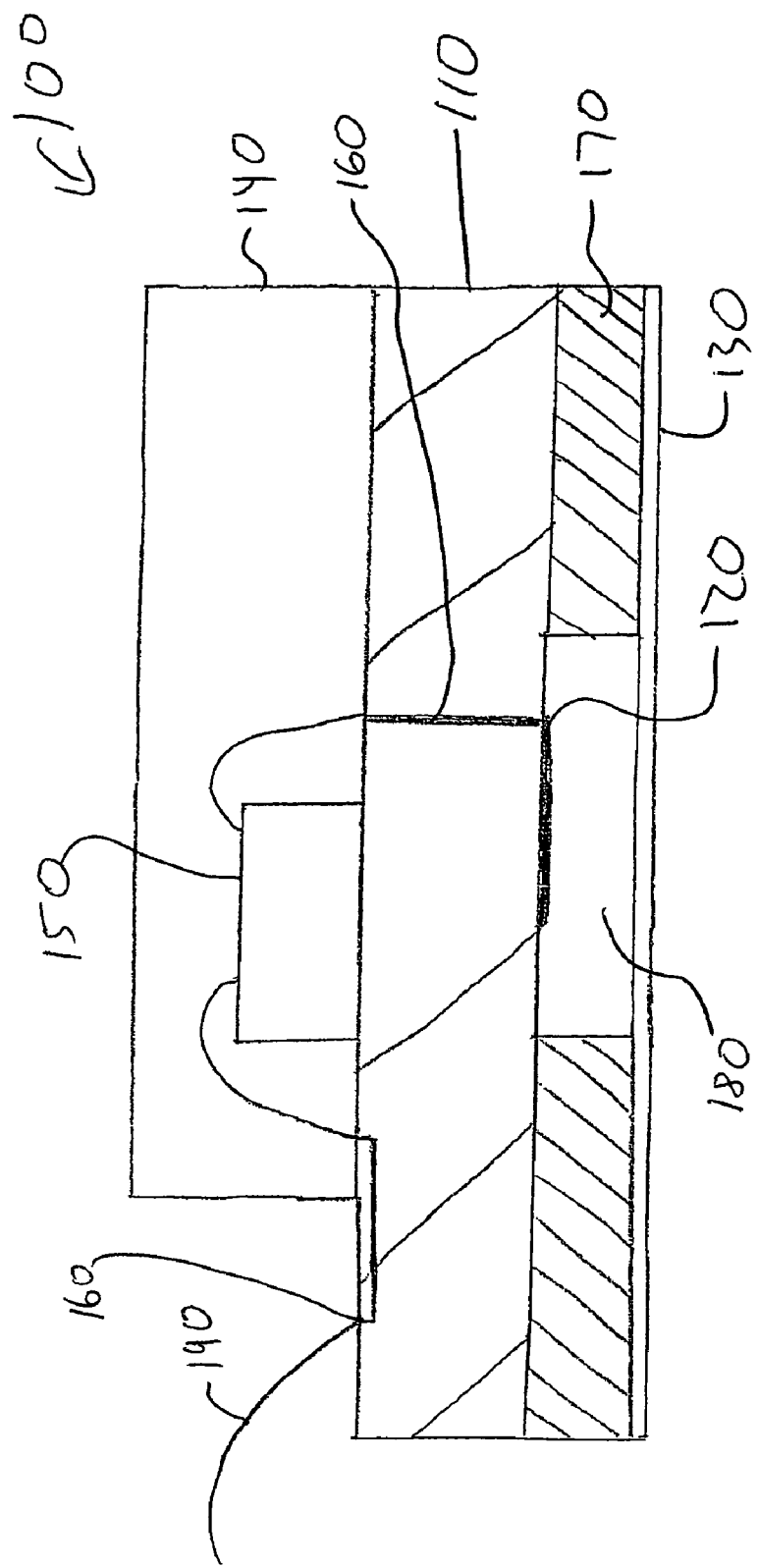
FIG. 5 is a side sectional view of an implantable capacitive pressure sensor in accordance with an embodiment of the invention.
Figure 6:
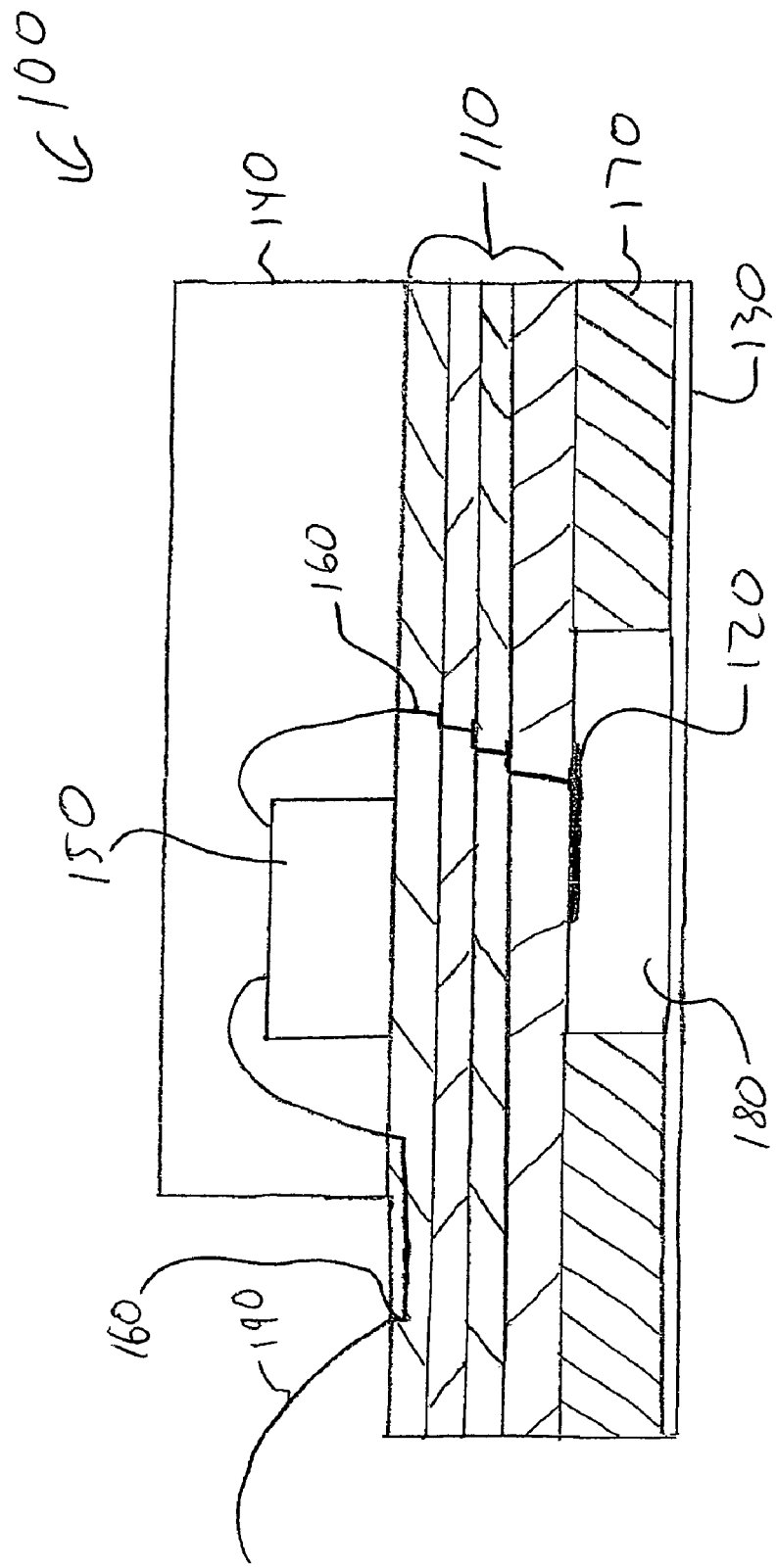
FIG. 6 is a side sectional view of an implantable capacitive pressure sensor in accordance with an embodiment of the invention.
Figure 7:
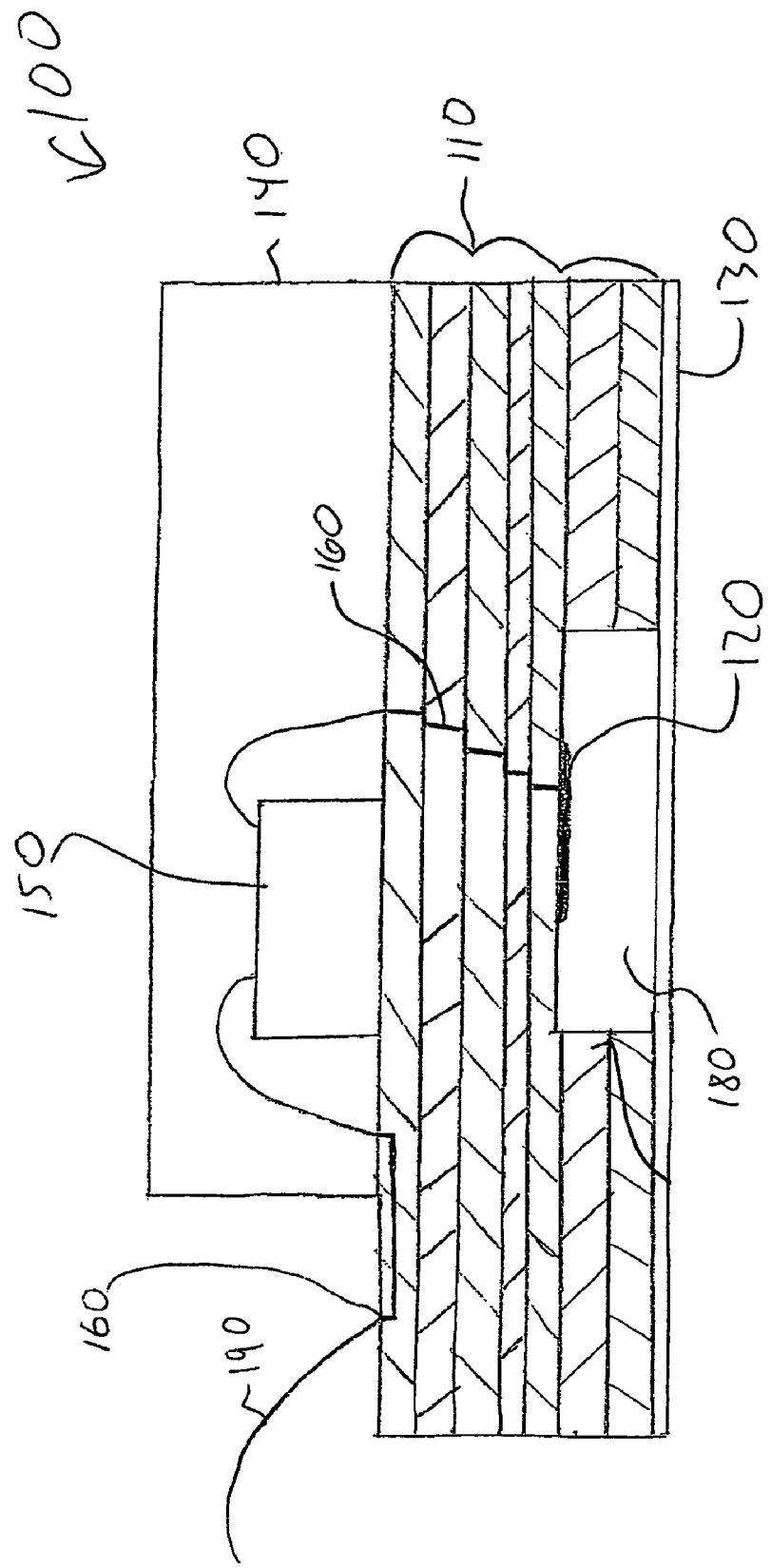
FIG. 7 is a side sectional view of an implantable capacitive pressure sensor in accordance with an embodiment of the invention.

The substrate 110 is shown in FIGS. 4-7 and may comprise any suitable material useful for providing insulative properties between the conductive plate 120 and the conductive diaphragm 130. For example, the substrate 110 may comprise ceramic. In some embodiments, the substrate 110 includes more than one layer of ceramic, as shown in FIGS. 6 and 7. In such embodiments, the ceramic layers may be substantially monolithic, that is, having no readily distinguishable layers of ceramic once formed. For example, the substrate 110 may comprise a high temperature cofired ceramic substrate or a low temperature ceramic substrate.

In some embodiments, the insulative substrate comprises a substantially monolithic device with integrated electrical functionality. In such embodiments, each layer of the ceramic may include one or more vias 160 to provide electrical communication between the conductive plate 120 and pressure sensing circuitry 150. Further, the via 160 in each layer may be at least partially offset from the via 160 of the adjacent layer to improve hermetic properties. In addition, this offset may be useful for accounting for different coefficients of expansion of the conductive and insulative materials. In such embodiments, the integrated electrical interconnects that comprise via and internal interconnects are constructed so as to provide a total resistance pathway suitable for low voltage DC or AC operation. For a given electrical interconnect structure utilizing cofired metallizations, the total resistance of the structure will be a function of the sheet resistance of the interconnect metallization and total area (number of squares), and the bulk resistivity of the via metallization and its geometry (length and cross-sectional area). Surface interconnect cofired metallizations may have sheet resistivities in the range of about 5-15 mOhm/sq. and the bulk resistance of the via metallization may be in the range of about 10-100 uOhmcm depending on the metal system. Standard via geometries may be in the range of about 4 mil to 10 mil diameter, with heights controlled by the starting ceramic layer thicknesses in the range of about 4 mil to 10 mil. Surface interconnect line widths may be in the range of about 5-40 mil or greater in width and length. It would be recognized by those skilled in the art that suitable low-voltage electrical pathways may be fabricated by various combinations of metals, surface interconnect and via geometries.

The conductive diaphragm 130 may comprise any suitable material. In some embodiments, the diaphragm 130 comprises a metal selected from the group consisting of gold, silver, copper, titanium, titanium alloys, and combinations or alloys thereof. In some embodiments the diaphragm 130 is adapted to directly contact bodily fluids (e.g., blood), such as by comprising a biocompatible and corrosion resistant material or by carrying a biocompatible coating, such as silicone. Further, the metal may be formed into a foil adapted to be displaceable in response to pressure changes of a magnitude experienced in a biologic environment.

Figure 9:
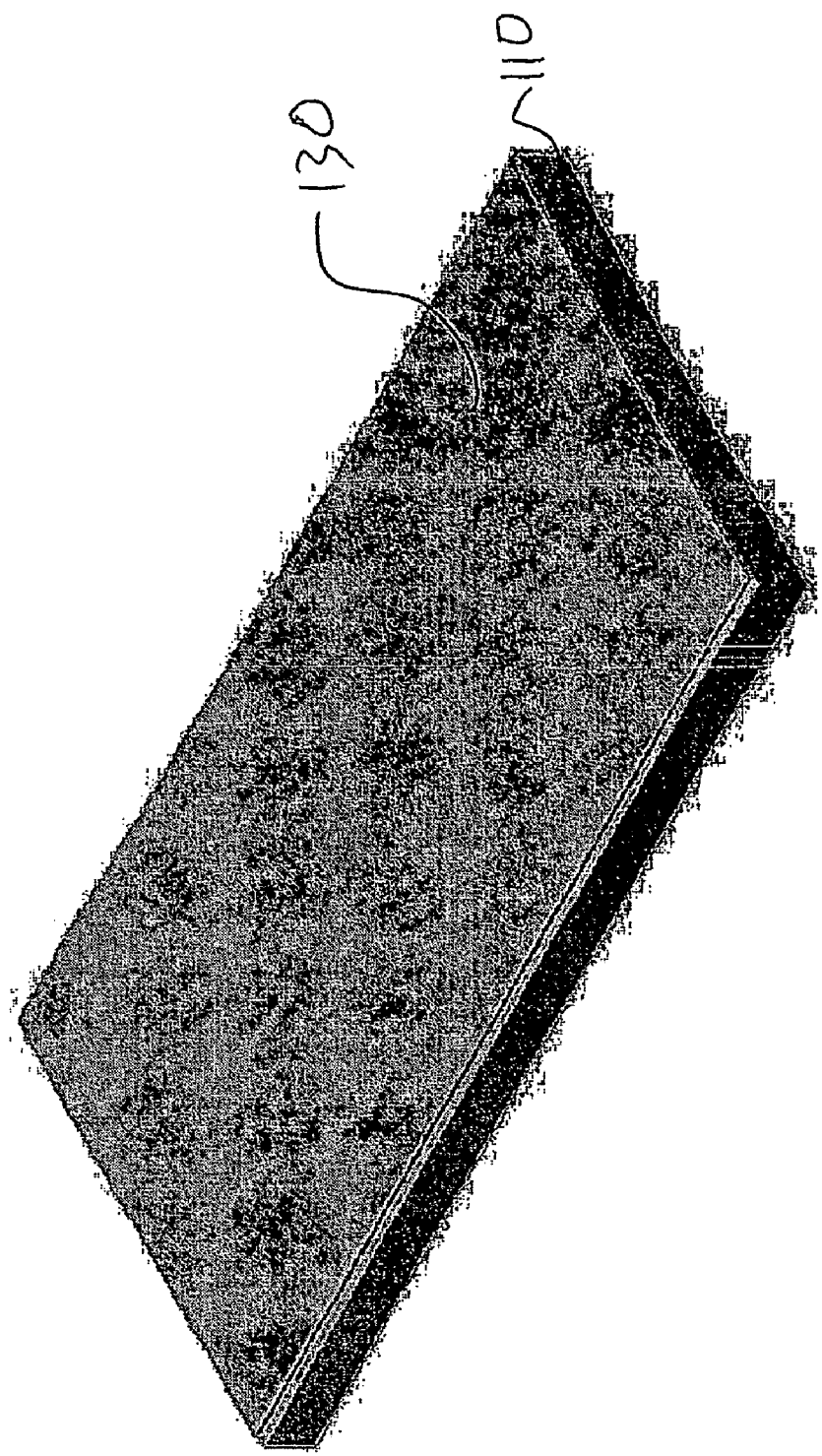
FIG. 9 is a perspective view of implantable capacitive pressure sensor components in accordance with an embodiment of the invention.
Figure 10:
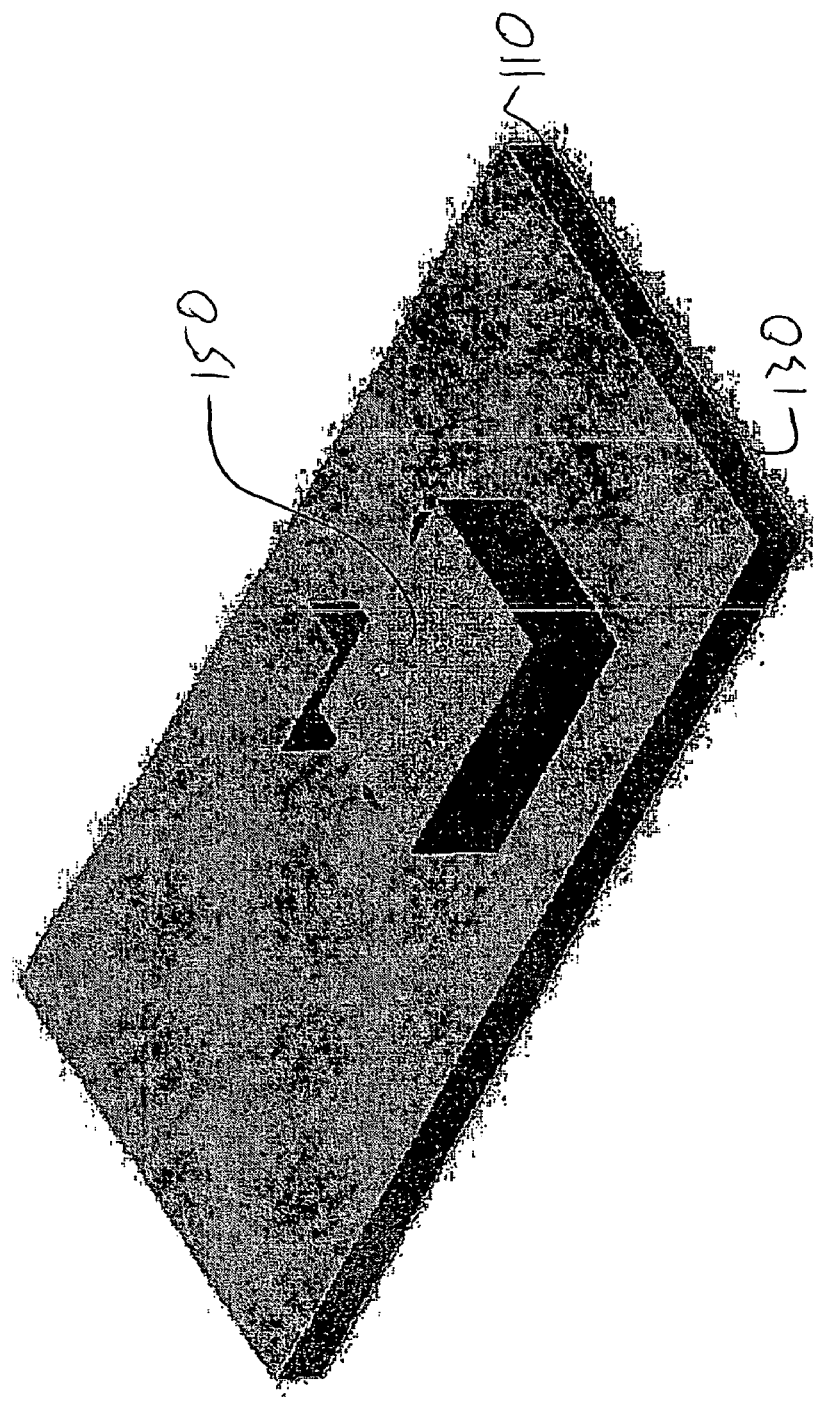
FIG. 10 is a perspective view of implantable capacitive pressure sensor components in accordance with an embodiment of the invention.

As shown in FIG. 9, the conductive diaphragm 130 may be functionally coupled to the substrate 110 by any suitable manner. For example, brazing, reactive metal brazing, diffusion bonding, and eutectic joint formation may be utilized. Further, the diaphragm 130 may be directly coupled to the substrate 110, or one or more interlayers 170 may be used. In embodiments including an interlayer 170, the diaphragm 130 may be coupled to the interlayer 170, which itself may be coupled to the substrate 110.

In some embodiments, the pieces are functionally coupled by brazing. Brazing may be defined as the joining of two pieces by fusing a layer of a brazing material (e.g., metal)

between adjoining surfaces of the pieces. Generally, the process involves a braze melting and flowing between the two pieces of material, commonly referred to as wetting. In embodiments having a diaphragm 130 including a metal and a substrate 110 including ceramic, the diaphragm 130 may be brazed to the ceramic using a high temperature braze process. The braze material may form an interlayer 170 that provides a suitable thermochemical and hermetic environment for capacitive pressure sensing.

In some embodiments, the pieces are formed by reactive metal brazing (RMB). RMB may utilize an individual RMB foil or the RMB may be formed directly on the substrate or on the diaphragm using a suitable thin-film deposition process.

In other embodiments the pieces are functionally coupled by diffusion bonding. Generally, diffusion bonding involves holding components under load at an elevated temperature in a protective atmosphere or vacuum. The loads used are usually below those that would cause macrodeformation of the pieces. Bonding operations may be performed under vacuum or in an inert gas atmosphere, or, in some embodiments, in air. Diffusion bonding may also include the use of interlayers and the formation of a transient liquid phase.

Further, in some embodiments, a eutectic joint may be formed. This is similar to other joining methods that include intimate contact and heat except the two materials that form the eutectic joint have a lower melt point than either substrate. Further, a eutectic joint may be formed in a localized fashion using laser energy since the pieces are not at an elevated temperature to form the bond. In such embodiments the stresses (e.g., due to TCE mismatch) at service temperature are less. The localized heat may also be provided by patterned resistors on the substrate or by inductively coupled metal traces.

As shown in FIGS. 5 and 6, in some embodiments the diaphragm 130 is spaced from the conductive plate 120 by interlayer 170. Interlayer 170 may be used to build up a functional capacitive gap 180 between the conductive plate 120 and the conductive diaphragm 130 making up the opposing plates of the capacitor. The interlayer 170 may comprise any suitable depositions and/or metallic preforms known in the art to enable the ceramic-metal joining process (brazing, RMB, diffusion bonding, or soldering) (e.g., gold, silver, copper, Ti—Ni reactive braze-alloys, Niobium, Nickel, titanium, and combinations or alloys thereof). In some embodiments, the interlayer comprises an oxide deposition to form an interlayer to which the diaphragm may be bonded. The oxide may comprise most any known biocompatible amorphous or polycrystalline metal oxide such as $Al_2O_3$, $ZrO_2$, or combinations thereof. The oxide may be deposited using suitable vacuum thin-film deposition technology such as conventional sputtering, reactive-enhanced sputtering, pulsed-laser deposition, CVD or MOCVD. Further, the interfacial material used to functionally couple the diaphragm 130 to the substrate 110 may itself form the interlayer 170 to provide the capacitive gap space 180.

As shown in FIG. 7, in some embodiments the diaphragm 130 is spaced from the conductive plate 120 by a recessed cavity 180 formed in the substrate 110. For example, in embodiments having a substrate 110 including ceramic, the capacitive gap 180 may be formed into one or more of the ceramic layers by any suitable means, such as a laser, ultrasonic cutting tool, and/or ceramic polishing. In some embodiments a multilayer ceramic technology is utilized to define the capacitive gap by forming a cavity within the top ceramic layer. The cavity height may initially be defined by the thickness of an individual ceramic green-tape layer (discussed further below). Following sintering, the cavity height is reduced by lapping and polishing the cavity side of the monolith to the required cavity depth. This technique takes advantage of the tight thickness tolerance typical for ceramic green tape materials to form the pre-cavity structure within the monolithic structure, and the close tolerance (e.g., <0.5 um) for typical precision lapping processes. In addition, this technique enables full integration of the capacitive pickup electrode and associated interconnect buried within the monolith.

Figure 7A:
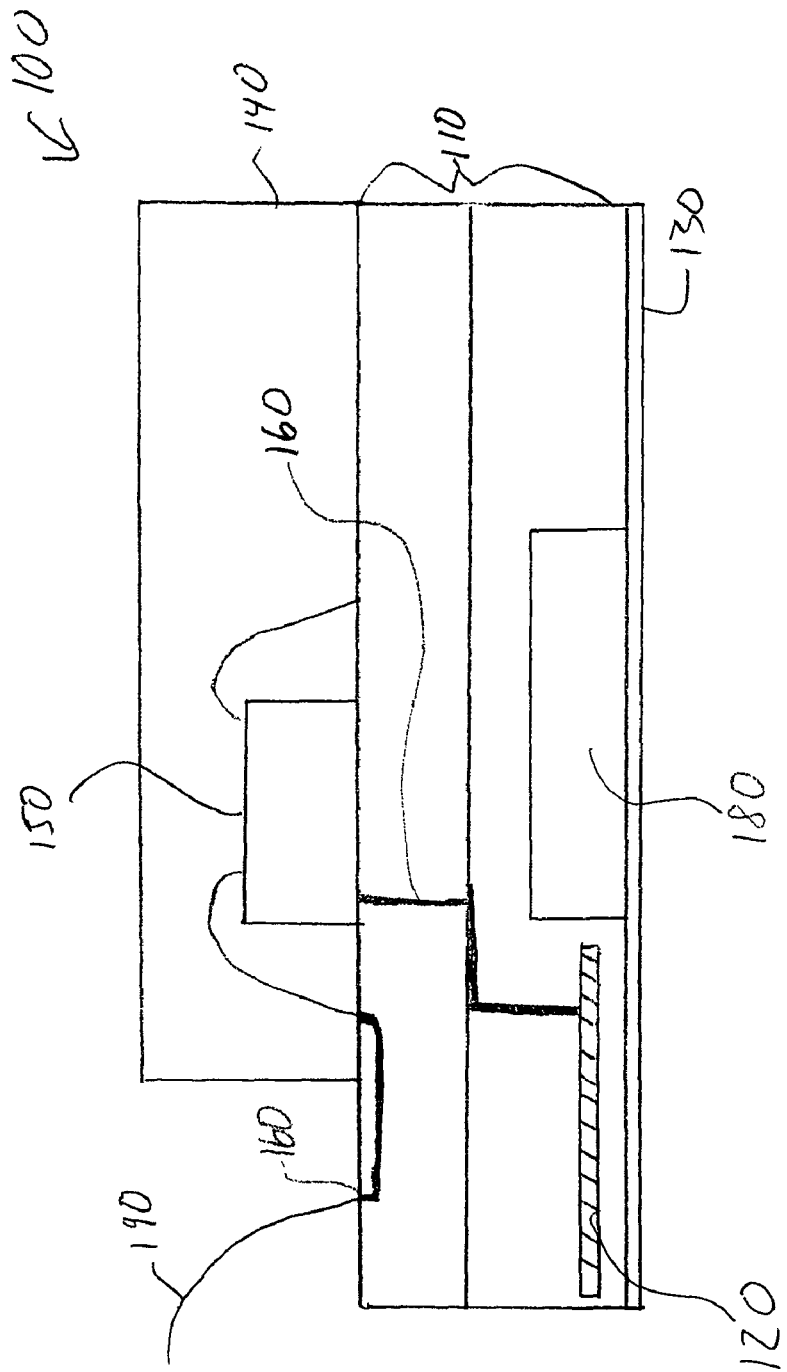
FIG. 7A is a side sectional view of an implantable capacitive pressure sensor in accordance with an embodiment of the invention.

In some embodiments, the interlayer 170 defining cavity 180 may be used as a dielectric for the conductive plate 120. In such embodiments, the layer to which the diaphragm 130 is bonded could be larger on one or more edges than required to support the diaphragm, and the conductive plate could be embedded between the substrate and the interlayer, as shown in FIG. 7A. A portion or all of the perimeter bond region of the diaphragm 130 to the interlayer could be used to embed the conducting plate 120. These embodiments offer several advantages. For example, where the interlayer 170 is formed of ceramic, the 10× permittivity of the interlayer relative to air allows for significant reduction in size of the conductive plate area and hence a reduction in sensor size. Further, these embodiments avoid placing the conductive plate in the area where the diaphragm is moving in response to pressure, thereby avoiding potential coupling of the pressure signal into the conductive plate.

Figure 8:
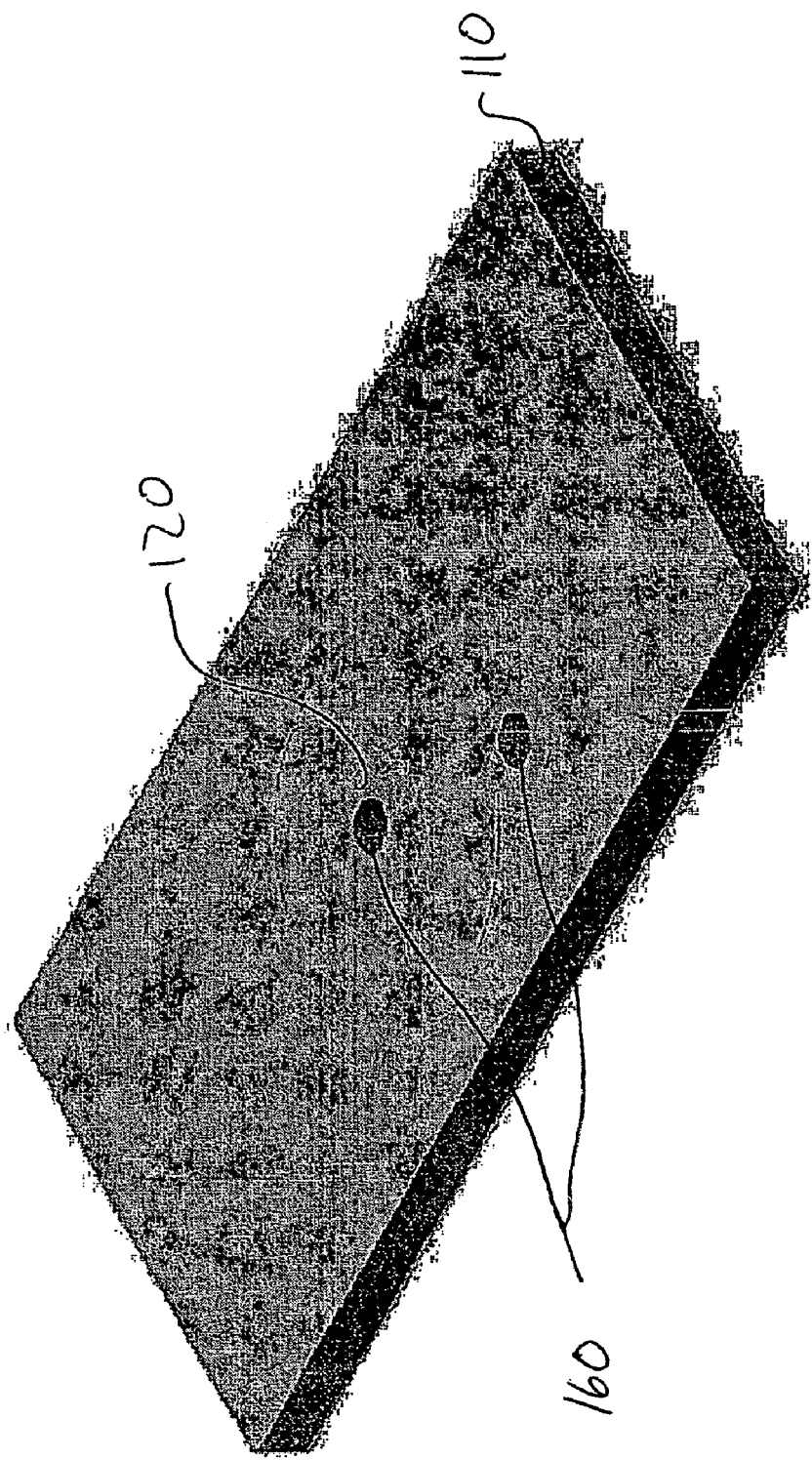
FIG. 8 is a perspective view of implantable capacitive pressure sensor components in accordance with an embodiment of the invention.

In some embodiments, the conductive plate 120 is functionally coupled to the substrate 110, as shown in FIG. 8. The conductive plate 120 may be functionally coupled to the substrate 110 by any suitable manner. For example, brazing or diffusion bonding may be used. Further, the conductive plate 120 may be a thin metallic plate that is printed on the substrate 110 surface. In some embodiments, the conductive plate 120 is formed integrally with the substrate 110, such as that derived from multilayer ceramic cofired technology. In one embodiment, the conductive plate may comprise a cofire metal formed from a screen-printed metal paste or a photo-defined metal ink. Alternatively, the metal plate may be a thin-film metallization formed after sintering of the substrate. The thin-film metallization may be formed using any vacuum deposition process known in the art, or may be formed using electroplating. Further, the conductive plate 120 may comprise a metal selected from the group consisting of gold, silver, copper, titanium, niobium, platinum, and combinations or alloys thereof.

The pressure sensing circuitry 150 may be any circuitry useful for monitoring static or differential pressure and is best shown in FIGS. 5-7 and 10. Pressure sensing circuitry may comprise an integrated circuit and may also include one or more discrete circuits. In some embodiments, the pressure sensing circuitry 150 receives a signal from the conductive plate 120 that may be used to determine a pressure. The circuitry 150 may receive the signal through one or more vias 160 integrated within the substrate 110. The pressure sensing circuitry 150 may then calculate the static or differential pressure based on, for example, a calibration curve. In some embodiments, the pressure sensing circuitry 150 may relay this signal to a medical device 10 or programming unit 20 where the pressure output is calculated. Further, a wireless transmitter may be in communication with the pressure sensing circuitry 150 for communicating pressure related data. The static or relative pressure value may be used for informational purposes or by the medical device 10 to determine or adjust a therapy.

Figure 3:
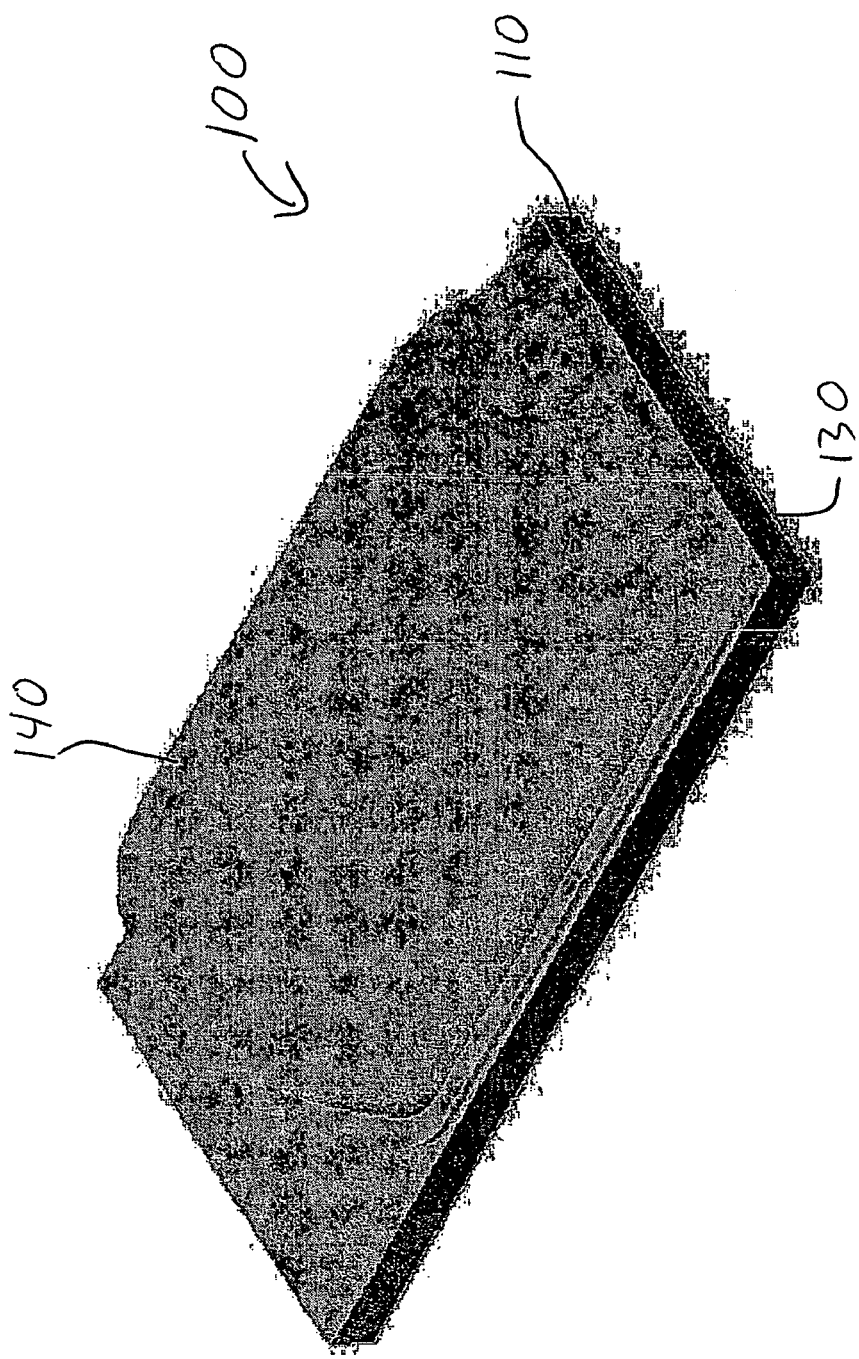
FIG. 3 is a perspective view of an implantable capacitive pressure sensor in accordance with an embodiment of the invention.
Figure 4:
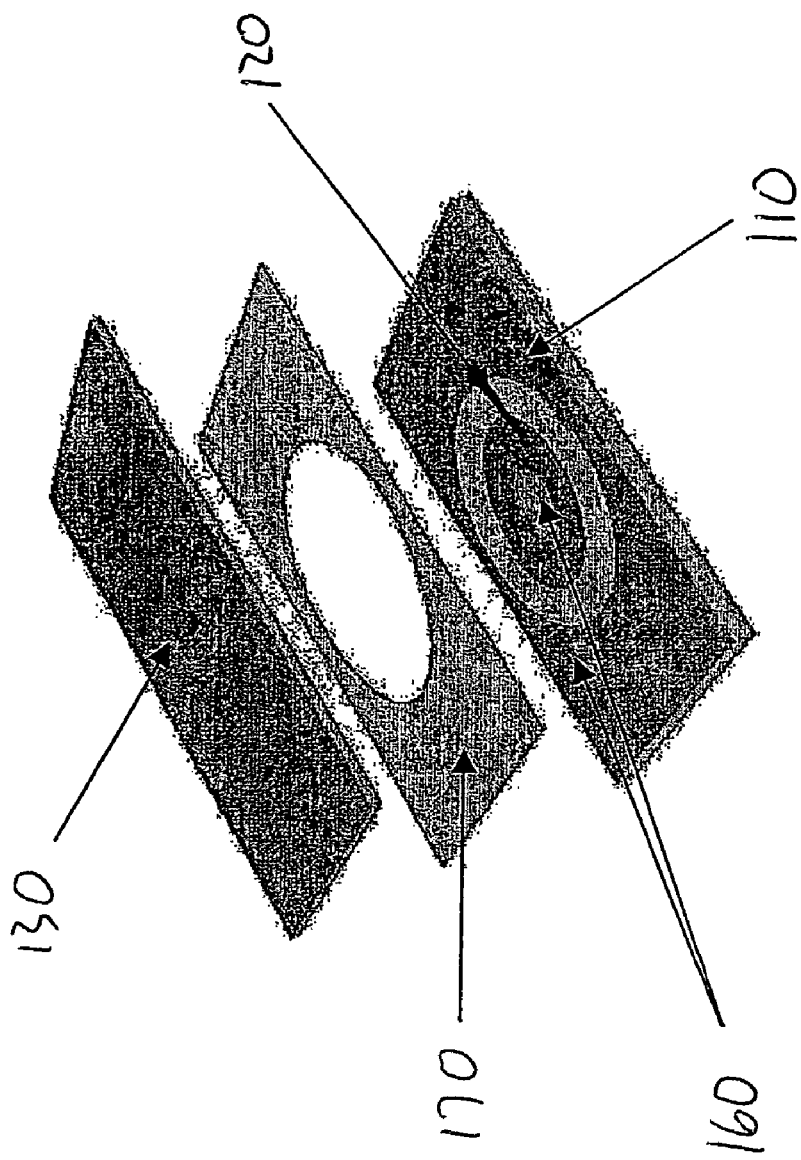
FIG. 4 is an exploded perspective view of implantable capacitive pressure sensor components in accordance with an embodiment of the invention.
Figure 11:
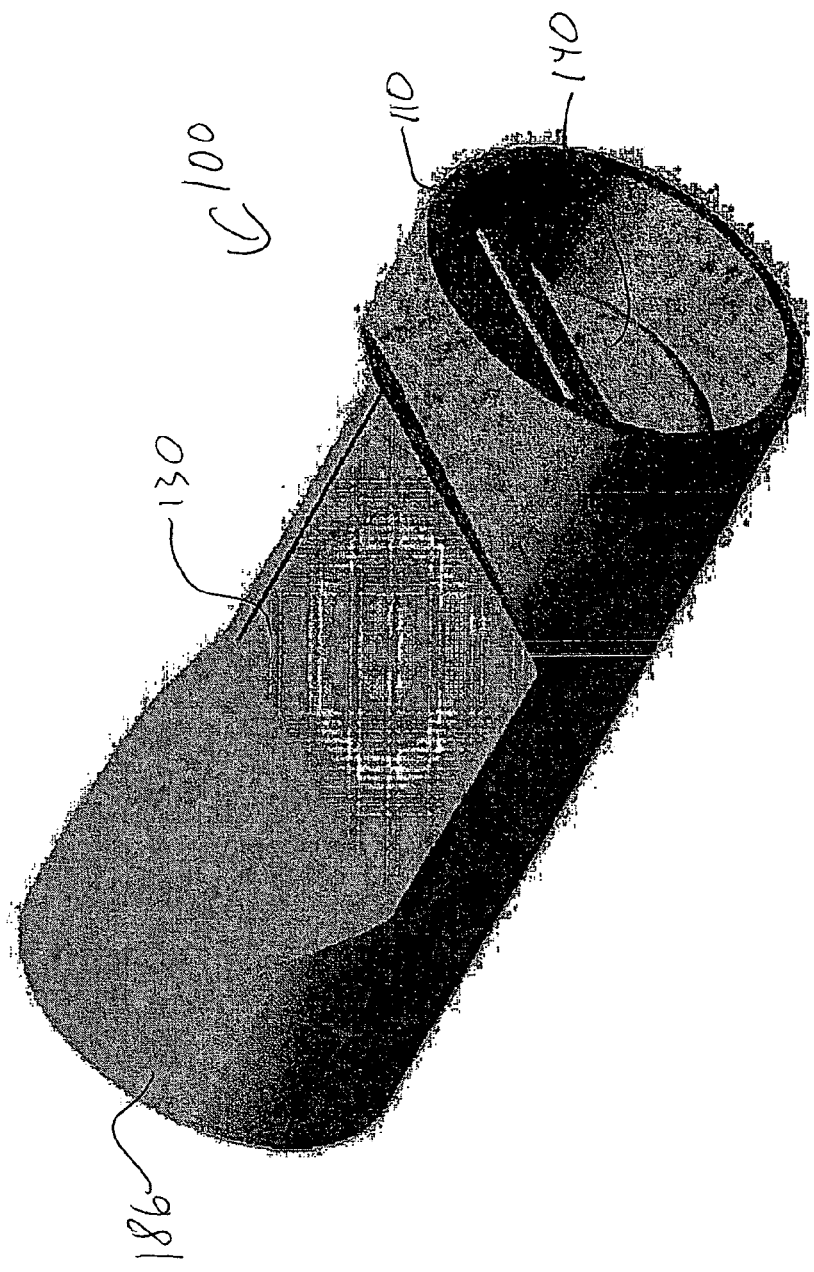
FIG. 11 is a partially cut-away perspective view of an implantable capacitive pressure sensor in accordance with an embodiment of the invention.

As shown in FIGS. 3 and 11, a lid 140 may be provided. Such a lid 140 may comprise any suitable material and be hermetically sealed to the substrate 110. Further, in some embodiments, the pressure sensing circuitry 150 may be disposed within a volume generally defined by the lid 140 and the substrate 110. This arrangement provides for a low profile capacitive sensor capsule 100 as the capacitor and circuitry 150 are provided within the same piece.

Some embodiments of the invention include a lead 14 provided with an implantable pressure sensor capsule 100 as described above. For example, the implantable pressure sensor capsule 100 may be disposed within a lumen defined by the lead body. As shown in FIG. 11, a housing 186 may be provided to house the capsule 100. In some embodiments, the housing 186 may have a shape adapted to fit within a lumen of lead 14 (e.g., generally cylindrical). Further, in some therapy leads (e.g., pacing and ICD), the housing 186 may also have one or more cut-out features or include a generally flat surface (e.g., a 'D" shape cross section) to allow for non-sensor conductor wires to pass the capsule. In addition, a wire 190 (as shown in FIGS. 5-7) may be provided to electrically connect the sensor capsule 100 to a medical device 10. Further, such a wire 190 may be disposed within the lumen of the lead 14.

Figure 12:
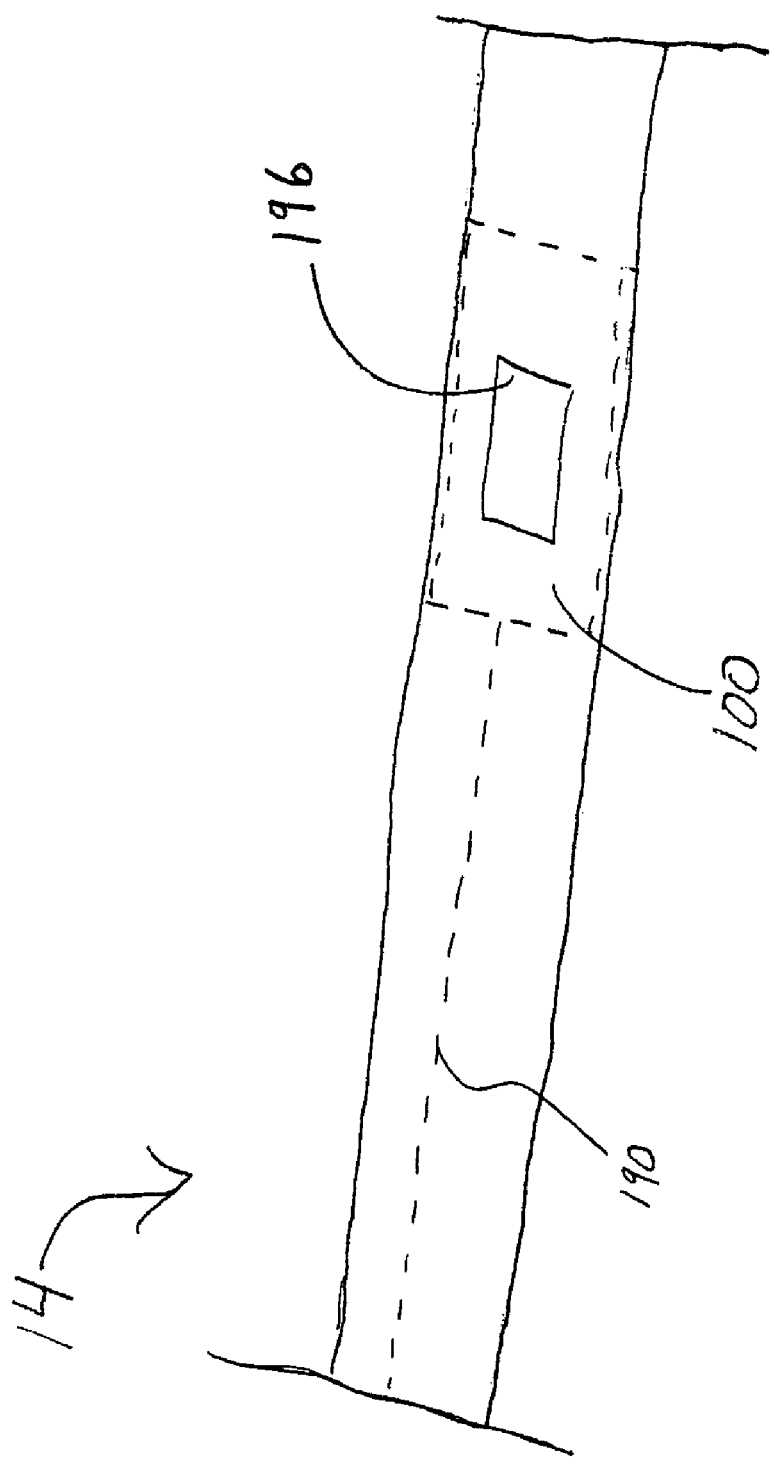
FIG. 12 is a hidden line view of an implantable capacitive pressure sensor disposed within a lumen of a lead in accordance with an embodiment of the invention.

In some embodiments the lead 14 body includes a window 196 (as shown in FIG. 12) adapted to allow bodily fluid (e.g., blood) to contact the diaphragm 130. In some embodiments, the diaphragm 130 is perpendicular to a longitudinal axis of the lead 14, such that the diaphragm 130 is disposed at the tip of the lead 14. Such embodiments allow the conductive diaphragm 130 to experience pressure imparted by the bodily fluid. In some embodiments, the window 196 can be covered with a non-compressible polymer (e.g., silicone). In such embodiments, the sensor may initially experience drift as the polymer gets saturated. Once stabilized, however, the polymer provides an iso-diameter lead to contribute to stable blood flow past the sensor, thereby reducing stagnation and clotting. The window 196 may also be covered with a hydrogel, which may reduce initial sensor drift.

The invention also includes a method of manufacturing a capacitive pressure sensor capsule 100. In some embodiments, a wafer of a substrate 110 and a conductive plate 120 may be provided. The ceramic wafer may be formed using multilayer ceramic technology using materials and processes known in the art. For example, multilayer ceramic technology is described in Richard E. Mistler, "Tape casting: The Basic Process for meeting the needs of the Electronics Industry", Ceramic Bulletin, Vol. 69 (6), pp-1022-26 (1990), the contents of which are hereby incorporated by reference.

The substrate may be formed using multilayer ceramic technology by using ceramic green-sheet layers that are sintered together to form a substantially monolithic structure. The green-sheet is typically a polymer-ceramic composite that is comprised of an organic (polymer) binder filled with glass, ceramic, or glass-ceramic or mixtures thereof. The organic binder may also contain plasticisers and dispersants. To form electrically conductive pathways, thick-film metal inks and pastes are used to form pre-cursor pathways that form electrically conducting pathways following cofireing. Thick-film pastes or inks may contain metal for formation of electrical pathways or dielectrics for formation of integrated passives such as resistors and capacitors. The organic vehicle may contain polymers, solvents and plasticisers. Thick-film technology is further described in J. D Provance, "Performance Review Of Thick Film Materials", Insulation/Circuits, (April 1977), and in Morton L. Topfer, "Thick-film Microelectronics, Fabrication, Design, and Applications (1977), pp. 41-59, the contents of each of which are hereby incorporated by reference.

Electrical interconnections across the substrate (i.e., in the X-Y plane) may be formed using metal thick-film inks with a texturing process such as screen-printing or photo-thick-film. Electrical interconnections through the substrate (i.e., in the Z plane) may be formed using metal thick-film pastes that are deposited within open vias formed in the ceramic green-tape. In some embodiments, the texturing process is applied using screen-printing technology. The screen-printing process utilizes a patterned silk-screen mask through which thick-film ink is forced to define the conductive pathway. Utilizing a metal plate with through holes, screen-printing can be used to define via interconnects by forcing metal pastes through the holes in the metal plate and into the ceramic vias. In some embodiments, after each layer is textured to form the necessary electrical interconnect circuitry, individual green-tape layers are aligned, laminated together, and then sintered to form a substantially monolithic ceramic structure with integrated electrical conduction pathways.

The conductive diaphragm 130 may be placed over the substrate 110 on the side facing the conductive plate 120, spaced from the conductive plate 120 and functionally coupled to the substrate 110. An interlayer 170 may be disposed between the substrate 110 and the diaphragm 130 to provide a capacitive gap 180, or, alternatively, the wafer may be provided with a cavity to provide the capacitive gap 180. The pressure sensing circuitry 150 for each individual sensor is disposed on a surface of the substrate 110 opposite to the conductive plate 120 and may be operatively connected to the conductive plate 120, and a lid 140 for each individual sensor is disposed over the circuitry 150 and may be hermetically sealed against the substrate 110 to enclose the pressure sensing circuitry 150. Further, the wafer may be diced to produce multiple individual capacitive pressure sensor capsules 100. Such a method is especially adapted to allow for relatively low cost and high volume manufacturing of pressure sensors suitable for use in biological environments.

Thus, embodiments of the IMPLANTABLE CAPACITIVE PRESSURE SENSOR SYSTEM AND METHOD are disclosed. One skilled in the art will appreciate that the invention can be practiced with embodiments other than those disclosed. The disclosed embodiments are presented for purposes of illustration and not limitation, and the invention is limited only by the claims that follow.

What is claimed is:

1. An implantable capacitive pressure sensor capsule comprising:
   a substrate;
   an interlayer coupled to a first surface of the substrate, wherein the interlayer is formed of ceramic;
   a conductive plate embedded within the substrate;
   a conductive diaphragm hermetically bonded to the interlayer;
   a lid hermetically sealed against a second surface of the substrate opposite the first surface; and
   pressure sensing circuitry disposed within a volume generally defined by the lid and the second surface of the substrate, wherein the pressure sensing circuitry is electrically coupled to the conductive plate.

2. A sensor capsule according to claim 1, wherein the substrate comprises at least two layers of ceramic to form a substantially monolithic substrate.

3. A sensor capsule according to claim 2, wherein each layer of the ceramic substrate_includes a via to provide electrical communication between the conductive plate and pressure sensing circuitry.

4. A sensor capsule according to claim 3, wherein the via in each layer of the ceramic substrate is at least partially offset from the via of the adjacent layer.

5. A sensor capsule according to claim 1, wherein the conductive plate and the diaphragm independently comprise a metal selected from the group consisting of gold, silver, copper, titanium, niobium, platinum, and combinations or alloys thereof.

6. A sensor capsule according to claim 1, wherein the diaphragm is functionally coupled to the substrate by one of brazing, reactive metal brazing, diffusion bonding, and eutectic joint formation.

7. A sensor capsule according to claim 1, wherein the diaphragm is adapted to contact bodily fluid.

8. A lead provided with an implantable pressure sensor capsule comprising:
- an elongated lead body having a window; and
- an implantable pressure sensor capsule integrated in the lead body, the pressure sensor capsule including;
  - a substrate;
  - an interlayer coupled to a first surface of the substrate, wherein the interlayer is formed of ceramic;
  - a conductive plate embedded within the substrate;
  - a conductive diaphragm hermetically bonded to the interlayer;
  - a lid hermetically sealed against a second surface of the substrate opposite the first surface; and
  - pressure sensing circuitry disposed within a volume generally defined by the lid and the second surface of the substrate, wherein the pressure sensing circuitry is electrically coupled to the conductive plate, and further wherein at least a portion of the conductive diaphragm is located in the window of the lead body where it is directly exposed to bodily fluids when the lead body is implanted in a body.

9. A lead according to claim 8, wherein the substrate comprises at least two layers of ceramic to form a substantially monolithic substrate.

10. A lead according to claim 9, wherein each layer of the ceramic substrate includes a via to provide electrical communication between the conductive plate and pressure sensing circuitry.

11. A lead according to claim 10, wherein the via in each layer of the ceramic substrate is at least partially offset from the via of the adjacent layer.

12. A lead according to claim 8, wherein the conductive plate comprises a cofired thick-film metallization over a via.

* * * * *